(12) United States Patent
Santoli et al.

(10) Patent No.: US 6,828,147 B1
(45) Date of Patent: Dec. 7, 2004

(54) METHOD OF MODIFYING CYTOTOXIC CELLS AND USES THEREOF

(75) Inventors: Daniela Santoli, Bryn Mawr, PA (US); Giovanni Rovera, Bryn Mawr, PA (US); Alessandra Cesano, Newburt Park, CA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 09/913,911
(22) PCT Filed: Feb. 23, 2000
(86) PCT No.: PCT/US00/04548
§ 371 (c)(1),
(2), (4) Date: Aug. 21, 2001
(87) PCT Pub. No.: WO00/50569
PCT Pub. Date: Aug. 31, 2000

Related U.S. Application Data
(60) Provisional application No. 60/121,482, filed on Feb. 24, 1999.

(51) Int. Cl.[7] .......................... C12N 5/00; C12N 5/02; C12N 5/08
(52) U.S. Cl. .................... 435/372; 435/372.3; 435/375; 435/377; 435/383; 435/386; 435/387
(58) Field of Search .............................. 435/372, 372.3, 435/375, 377, 383, 386, 387

(56) References Cited

U.S. PATENT DOCUMENTS

| | | |
|---|---|---|
| 5,126,132 A | 6/1992 | Rosenberg |
| 5,272,082 A | 12/1993 | Santoli et al. |
| 5,660,824 A | 8/1997 | Grabstein |
| 5,683,690 A | 11/1997 | Santoli et al. |
| 5,702,702 A | 12/1997 | Santoli et al. |
| 5,747,024 A | 5/1998 | Grabstein |
| 5,820,856 A | 10/1998 | Santoli et al. |
| 6,022,538 A | 2/2000 | Santoli |

FOREIGN PATENT DOCUMENTS

| | | |
|---|---|---|
| WO | WO94/26284 A1 | 11/1994 |
| WO | WO95/27722 A1 | 10/1995 |
| WO | WO98/48630 A1 | 11/1998 |

OTHER PUBLICATIONS

A. Gamero et al, "Interleuin 15 Induction of Lymphokine-activated Killer Cell Function Against Autologous Tumor Cells in Melanoma Patient Lymphocytes by a CD18–Dependent, Perforin–related Mechanism", Cancer Research, 55:4988–4994 (Nov., 1995).
A. Cesano et al, "Two Unique Human Leukemic T–Cell Lines Endowed with a Stable Cytotoxic Function and a Different Spectrum of Target Reactivity Analysis and Modulation of Their Lytic Mechanisms", In Vitro Cell. Dev. Biol., 28A:648–656 (Sep.–Oct., 1992).
A. Cesano et al, "Effects of Lethal Irradiation and Cyclosporin A Treatment on the Growth and Tumoricidal Activity of a T Cell Clone Potentially Useful in Cancer Therapy", Cancer Immunol. Immunother., 40:139–151 (1995).
D. Santoli et al, "Synergistic and Antagonistic Effects of IL–1α and IL–4, Respectively, on the IL–2–Dependent Growth of a T Cell Receptor–γδ+Human T Leukemia Cell Line", J. Immunol., 144(12):4703–4711 (Jun., 1990).
J. Disanto, "Cytokines: Shared Receptors, Distinct Functions", Current Biology, 7:R424–R426 (Jul., 1997).
B. Rouse et al, "Consequences of Exposure to Ionizing Radiation for Effector T Cell Function in Vivo", Viral Immunology, 2(2):69–78 (1989).
T. Han et al, "Stimulating Capacity of Blast Cells from Patients with Chronic Myelocytic Leukaemia, in Blastic Crisis in 'one–way' Mixed Lymphocyte Reaction: Lack of Evidence for T Lymphoblastic Conversion", Immunology, 35:299–305 (1978).
K. Foon, "Biological Response Modifiers: The New Immunotherapy", Cancer Research, 49:1621–1639 (Apr., 1989).
T. Boon, "Tumor Antigens Recognized by Cytolytic T Lymphocytes: Present Perspectives for Specific Immunotherapy", Int. J. Cancer, 54:177–180 (1993).
M. Osband et al, "Problems in the Investigational Study and Clinical Use of Cancer Immunotherapy", Immunology Today, 11(6):103–105 (1990).
A. Cesano et al, "Phase I Clinical Trial with a Human Major Histocompatibility Complex Nonrestricted Cytotoxic T–Cell Line (Tall–104) in Dogs with Advanced Tumors", Cancer Research, 56:3021–3029 (Jul., 1996).
R. O'Connor et al, "Growth Factor–Dependent Differentiation Along the Myeloid and Lymphoid Lineages in an Immature Actue T Lymphocytic Leukemia", J. Immunol., 145(11):3779–3787 (Dec., 1990).
S. Chan et al, "Mechanisms of IFN–γ Induction by Natural Killer Cell Stimulatory Factor (NKSF/IL–12)", J. Immunol., 148(1):92–98 (Jan. 1992).
R. O'Connor et al, "Growth Factor Requirements of Childhood Acute T–Lymphoblastic Leukemia: Correlation Between Presence of Chromosomal Abnormalities and Ability to Grow Permanently In Vitro", Blood, 77(7):1534–1545 (Apr., 1991).
A. Cesano et al, "Cellular and Molecular Mechanisms of Activation of MHC Nonrestrited Cytotoxic Cells by IL–12", 151:2943–2957 (1993).

(List continued on next page.)

*Primary Examiner*—Christina Chan
*Assistant Examiner*—Marianne DiBrino
(74) *Attorney, Agent, or Firm*—Howson and Howson

(57) ABSTRACT

TALL-104 cells, and other cytotoxic T cell lines, may be modified to increase the cytotoxicity thereof, to enhance growth properties, and/or to provide a preferred phenotype, e.g., expression of cell surface antigens, function, e.g., change in cytokine production profile, by culturing the cells in an effective amount of IL-15, optionally followed by gamma irradiation to halt proliferation.

5 Claims, 16 Drawing Sheets

OTHER PUBLICATIONS

S. Visonneau et al, "A Revertant TCRγδ+ Cell Clone Which has Cost MHC Nonrestricted Cytotoxic Activity but Retains Redirected killing Upon Stimulation of the CD3 Receptor", Cell. Immunol., 165:252–265 (1995).

A. Cesano et al, "Role of CD38 and its Ligand in the Regulation of MHC–Nonrestricted Cytotoxic T Cells", J. Immunol., 160:1106–1115 (1998).

J. Giri et al, "IL–5, a Novel T Cell Growth Factor that Shares Activities and Receptor Components with IL–2", J. Leuko. Biol., 57(5):763–766 (May, 1995).

L. Quinn et al, Interleukin–15: A Novel Anabolic Cytokine for Skeletal Muscle, Endocrinol., 136(8):3669–3672 (Aug., 1995).

W. Carson et al, "Endogenous Production of Interleukin 15 by Activated Human Monocytes is Critical for Optimal Production of Interferon–gamma by Natural Killer Cells in Vitro", J. Clin. Invest., 96(6):2578–2582 (Dec., 1995).

J. Jonuleit et al, "Induction of IL–15 Messenger RNA and Protein in Human Blood–Derived Dendritic Cells", J. Immunol., 158(6):2610–2615 (Mar., 1997).

V. Garcia et al, "IL–15 Enhances the Response of Human γδ T Cells to Nonpeptide Microbial Antigens", J. Immunol., 160(9):4322–4329 (May, 1998).

A. Mori et al, "IL–15 Promotes Cytokine Production of Human T Helper Cells", J. Immunol., 156(7):2400–2405 (Apr., 1996).

M. Nieto et al., Interleukin–15 Induces Adhesion Receptor Redistribution in T Lymphocytes, Euro. J. Immunol., 26(6):1302–1307 (Jun., 1996).

M. Kennedy et al, "Characterization of Interleukin–15 (IL–15) and the IL–16 Receptor Complex", J. Clin. Immunol., 16(3):134–143 (May, 1996).

A. Angiolillo et al, "Interleukin–15 Promotes Angiogenesis in Vivo", Biochem. Biophys. Res. Comm., 233(1):231–237 (Apr., 1997).

P. Allavena et al, "IL–15 is Chemotactic for Natural Killer Cells and Stimulates their Adhesion to Vascular Endothelium", J. Leuko. Biol., 61(6):729–735 (Jun., 1997).

R. Evans et al, IL–15 Mediates Anti–tumor Effects after Cyclophosphamide Injection of Tumor–Bearing Mice and Enhances Adoptive Immunotherapy: The Potential Role of NK Cell Subpopulations, Cell. Immunol., 179(1):66–73 (Jul., 1997).

W. Carson et al, "Interluekin (IL) 15 is a Novel Cytokine that Activates Human Natural Killer Cells via Components of the IL–2 Receptor", J. Exp. Med., 180(4):1395–1403 (1994).

H. Kanegane et al, "Activation of Naive and Memory T Cells by Interleukin–15", Blood, 88(1):230–235 (Jul., 1996).

METHOD OF MODIFYING CYTOTOXIC CELLS AND USES THEREOF

CROSS-REFERENCE TO RELATED APPLICATIONS

This is a 371 of PCT/US00/04548, filed Feb. 23, 2000 which claims the benefit of the priority of U.S. patent application Ser. No. 60/121,482, filed Feb. 24, 1999.

FIELD OF THE INVENTION

The invention relates generally to the modification of cytotoxic T cells by treatment with a selected cytokine, and to the use of such modified cells in cancer therapy.

BACKGROUND OF THE INVENTION

The human T cell line TALL-104 (CD3/TCRαβ*CD8*CD16⁻) [A. Cesano et al, *In Vitro Cell. Dev. Biol.*, 28A:648 (1992); A. Cesano et al, *J. Immunol.*, 151:2943–2957 (1993); and A. Cesano et al, *Cancer Immunol, Immunoth.*, 40:139 (1995)] is endowed with MHC non-restricted killer activity and has been reported as useful, when lethally irradiated, against a broad range of tumors across several species, while sparing cells from normal tissues. As taught by the inventors' prior publications and patents cited above, unmodified TALL-104 cells are available from the American Type Culture Collection, 10801 University Boulevard Manassas, Va. 20110-2209 under Accession Number CRL 11386 and are described in U.S. Pat. No. 5,272,082. These cells may be preferably modified by lethal γ-irradiation and/or by stimulation in the cytokine interleukin 2 (IL-2) or Interleukin 12 (IL-12) to provide them with an increased cytotoxicity against tumor and virus-infected targets.

Such modification methods have been described in detail in International Patent Publication No. WO94/26284, published Nov. 24, 1994, which is incorporated by reference herein. For example, one modification step includes in vitro treatment of the TALL-104 cells with one or both of the two interleukins, recombinant human (rh) IL-2 and rhIL-12. When used independently to treat the cell line, IL-2 and IL-12 can induce the cell line's cytotoxic activity. When these cytokines are used together to modify the cell line, the modified cell line displays additive or increased cytotoxic effects. This results in a significant increase in cytotoxic activity and recycling capability, ultimately leading to 100% elimination of tumor targets at an E:T ratio<0.1:1 [Cesano et al, *J. Immunol.*, 151:2943 (1993)].

Another known modification step involves the exposure of the TALL-104 cell line to lethal irradiation to confer irreversible loss of growth capability with full retention of cytotoxic activity, both in vitro and in vivo. This is achieved by subjecting the cell line to γ-irradiation just prior to its use. Preferably, the cells are irradiated at 4000 rads using a $^{137}$Cs source. As described in International Patent Publication No. WO94/26284, irradiation of TALL-104 cells provides a modified cytotoxic cell line that has lost its proliferative ability and, therefore, the possibility of growing in an unrestrained fashion in the rag, recipient organism. These modified TALL-104 cells have been used in methods for the treatment of various cancers in humans and animals. See, also, U.S. Pat. Nos. 5,683,690; 5,702,702 and 5,820,856, and International patent publication No. WO98/48630, all incorporated herein by reference.

Other cytotoxic cells have also been described, such as the TALL-103/2 cells. See, U.S. Pat. No. 5,272,082 and A. Cesano et al, *J. Immunol*, 151:2943–2957 (1993); S. Visonneau et al, *Cell Immunol.*, 165:252–265 (1995); and A. Cesano et al, *J. Immunol.*, 160:1106–1115 (1998). However, TALL-103/2 cells, stimulated with IL-2 or IL-12, have been noted to have a limited spectrum of tumor target reactivities and display low levels of killing. These cells do not grow in severe combined immuno-deficient (SCID) mice. Thus, at present, TALL-103/2 cells have not appeared promising for clinical use.

Among the known cytokines, Interleukin-15 (IL-15) is a relatively novel T cell growth factor that shares some activities and receptor components with IL-2 [U.S. Pat. No. 5,747,024; J. G. Giri et al, *J. Leuko. Biol.*, 57(5):763–6 (May 1995); L. S. Quinn et al, *Endocrinol.*, 136(8):3669–72 (August 1995)]. IL-15 utilizes the β and γ chains of the IL-2 receptor for signal transduction, but uses a different subunit (α) to bind to the cells. The expression pattern of IL-15 α receptor is distinct from that of IL-2 α receptor. IL-15 has been shown to induce LAK cell functions in vitro at high doses of about 100 ng/ml by a CD18-dependent, perforin-related mechanism [A. M. Gamero et al, *Cancer Res.*, 55(21):4988–94 (November 1995)]. IL-15 is produced by monocytes and dendritic cells and has been shown to induce cytokine production in human T helper cells, and adhesion receptor redistribution in T lymphocytes. It has been described to stimulate proliferation of γδ T cells and act synergistically with other stimuli in inducing lymphokine production thereby [See, also, W. E. Carson et al, *J. Clin. Invest.* 96(6):2578–82 (December 1995); H. Jonuleit et al, *J. Immunol.*, 158(6):2610–5 (Mar. 15, 1997); V. E. Garcia et al, *J. Immunol.*, 160(9):4322–9 (May 1998); A. Mori et al, *J. Immunol* 156(7):2400–5 (April 1996); M. Nieto et al, *Euro. J. Immunol.*, 26(6):1302–7 (June 1996); M. K. Kennedy et al, *J. Clin. Immunol.*, 16(3):134–43 (May 1996)]. IL-15 has also been described as a vaccine adjuvant [U.S. Pat. No. 5,747,0241], a therapeutic [U.S. Pat. No. 5,660,824], and an inducer of angiogenesis [A. L. Angiolillo et al, *Biochem. Biophys. Res. Comm.*, 2(1):231–7 (Apr. 7, 1997)]. IL-15 has been said to have IL-2-like stimulating activities on T lymphocytes and NK cells [P. Allavena et al, *J. Leuko. Biol.*, 61(6):729–35 (June 1997); J. P. DiSanto, *Current Biol.*, 7(7):R424–6 (Jul. 1, 1997); R. Evans et al., *Cell. Immunol.*, 179(1):66–73 (Jul. 10, 1997)].

There exists a need in the art for methods for further enhancing the characteristics of cytotoxic T cells useful for therapy.

SUMMARY OF THE INVENTION

In one aspect, the invention provides a method of modifying, or reversibly modifying, the phenotype and function of cytotoxic T cells while retaining the cytotoxicity of the cells comprising the steps of:

(a) culturing said cells in an effective amount of IL-15 thereby obtaining a high yield of a cell having a first phenotype;

(b) culturing the IL-15 stimulated cells in an effective amount of IL-2, thereby altering the first phenotype to a second phenotype; and (c) optionally repeating steps (a) and (b) a selected number of times.

In another aspect, the invention provides a method of modifying a cytotoxic T cells while retaining the cytotoxicity of the cells comprising the steps of:

(a) culturing said cells in an effective amount of IL-2, thereby obtaining a first modified cell;

(b) culturing the IL-2 stimulated cells in an effective amount of IL-15; thereby obtaining a second modified cell; and (c) optionally repeating steps (a) and (b) a selected number of times.

The first and second modified cells from either method above demonstrate a change in at least one characteristic, such as increased proliferation, differentiation, growth, phenotype, adhesion molecule expression, biodistribution, cytokine production profile, level of cytotoxic activity, and tumor target spectrum. Desirably the cells are TALL-104 cells or TALL-103/2 cells.

In one embodiment of the first method, TALL-104 cells are cultured in an effective amount of IL-15, wherein said cells grow at a rate faster than when stimulated by IL-2, and have an altered phenotypic profile; and then the IL-15 stimulated TALL-104 cells are cultured in an effective amount of IL-2. In an embodiment of the second embodiment, the modification of cell characteristics is accomplished by first culturing TALL-104 cells in an effective amount of IL-2 and then culturing the IL-2 stimulated TALL-104 cells in an effective amount of IL-15.

In yet another aspect, the invention provides a method of modifying TALL-104 cells comprising culturing TALL-104 cells in an effective amount of IL-15, wherein said cells grow at a rate faster than when stimulated by IL-2, and have an altered phenotypic, cytotoxic and cytokine profile. The modified cells have an increased level of cytotoxicity or another change in a characteristic such as increased proliferation, differentiation, growth, phenotype, adhesion molecule expression, biodistribution, cytokine production profile, and tumor target spectrum. In one embodiment of this method the cytokine profile includes increased expression of IL-10, GM-CSF, TNF-α and TNF-5 and decreased expression of gamma interferon (IFN-γ) by the modified TALL-104 cells. In another embodiment, the modified phenotype includes increased expression of the cytotoxic adhesion/activation marker CD56 and/or decreased expression of the adhesion molecule CD38.

In still another aspect, the invention provides a method for increasing the levels of cytotoxic activity and spectrum of tumor target recognition of TALL-103/2 cells comprising culturing TALL-103/2 cells in an effective amount of IL-15, wherein said cells grow at a faster rate and have an expanded tumor target spectrum of cytotoxicity than when stimulated by IL-2.

In yet a further aspect, the invention provides modified TALL-104 cells, which are produced by stimulating said cells in an effective amount of IL-15.

In another aspect, the invention provides modified TALL-103/2 cells having an increased cytotoxicity, which are produced by stimulating said cells in an effective amount of IL-15.

Other aspects and advantages of the present invention are described further in the following detailed description of the preferred embodiments thereof.

DETAILED DESCRIPTION OF THE INVENTION

Cytotoxic T cell lines, such as TALL-104, have found use in clinical settings, such as the treatment of cancers, when administered in vivo, or when employed in ex vivo therapeutic regimens. Still other cytotoxic T cell lines, such as TALL-103/2 could be clinically useful if their target specificity was broadened and their growth in culture improved. The inventors have now discovered novel methods for increasing the cytotoxicity of these cells, altering their phenotypes and spectrum of target recognition, and, increasing their yield in culture.

Such modifications can be introduced to TALL-104 or TALL-103/2 cells, and are anticipated to be introduced to other cytotoxic T cells by stimulating the cells in IL-15, rather than, or in addition to, IL-2. Such IL-15 stimulation may optionally be followed by exposing the stimulated TALL-104 cell line to lethal irradiation to confer irreversible loss of growth capability with retention of cytotoxic activity, both in vitro and in vivo. This may be achieved by subjecting the cell line to γ-irradiation just prior to its use. Preferably, the cells are irradiated at 4000 rads using a $^{137}$Cs source, similar to the process described in International Patent Publication No. WO94/26284. Such irradiation of the IL-15 stimulated TALL-104 cells provides a modified cytotoxic cell line that has lost its proliferative ability and, therefore, the possibility of growing in an unrestrained fashion in the recipient organism.

Figure 2:
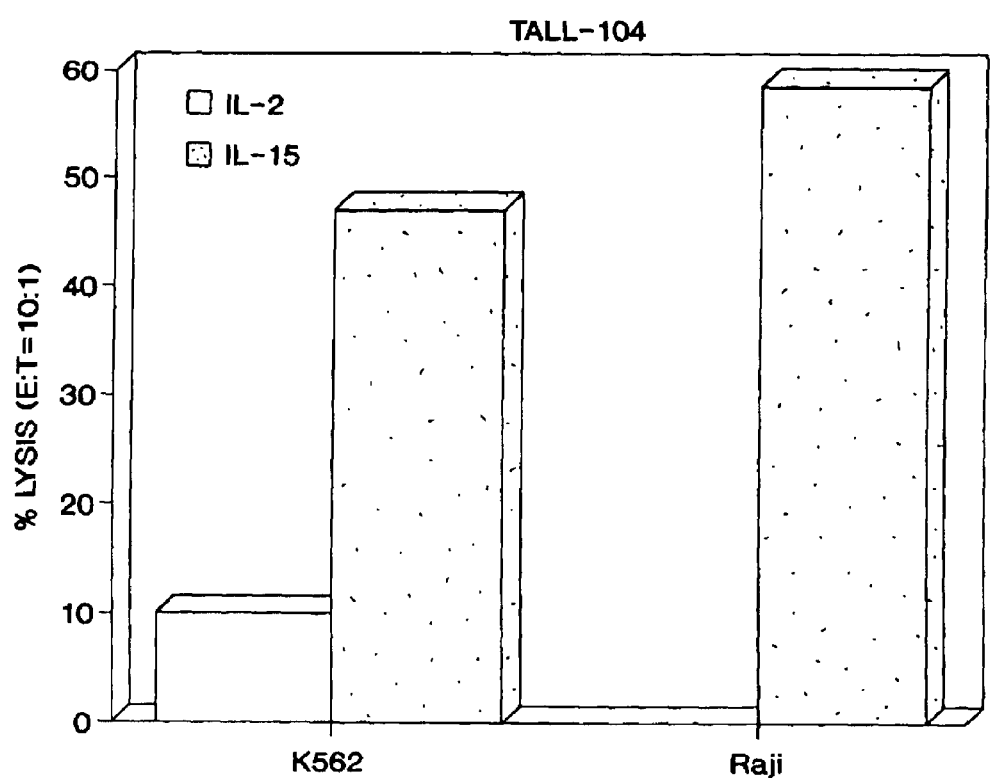
FIG. 2 is a bar graph illustrating that upon expansion of TALL-104 cells in vivo in SCID mice and re-adaptation to tissue culture conditions, IL-15 induces quicker differentiation of TALL-104 cells into cytotoxic cells in comparison to the effects of IL-2. Undifferentiated TALL-104 cells, extracted from SCID mouse spleens, were cultured for one week with either IL-2 or IL-15, and then tested for cytotoxicity against either K562 or Raji tumor cells. Cytotoxicity is demonstrated by percent lysis of the tumor cells. The open bar indicates IL-2 treatment; the strippled bar indicates IL-15 treatment. TALL-104 cells stimulated in IL-15 also show higher levels of cytotoxic molecules such as perforin, serine esterases (SE) and TIA-1, an apoptosis inducing molecule.
Figure 3:
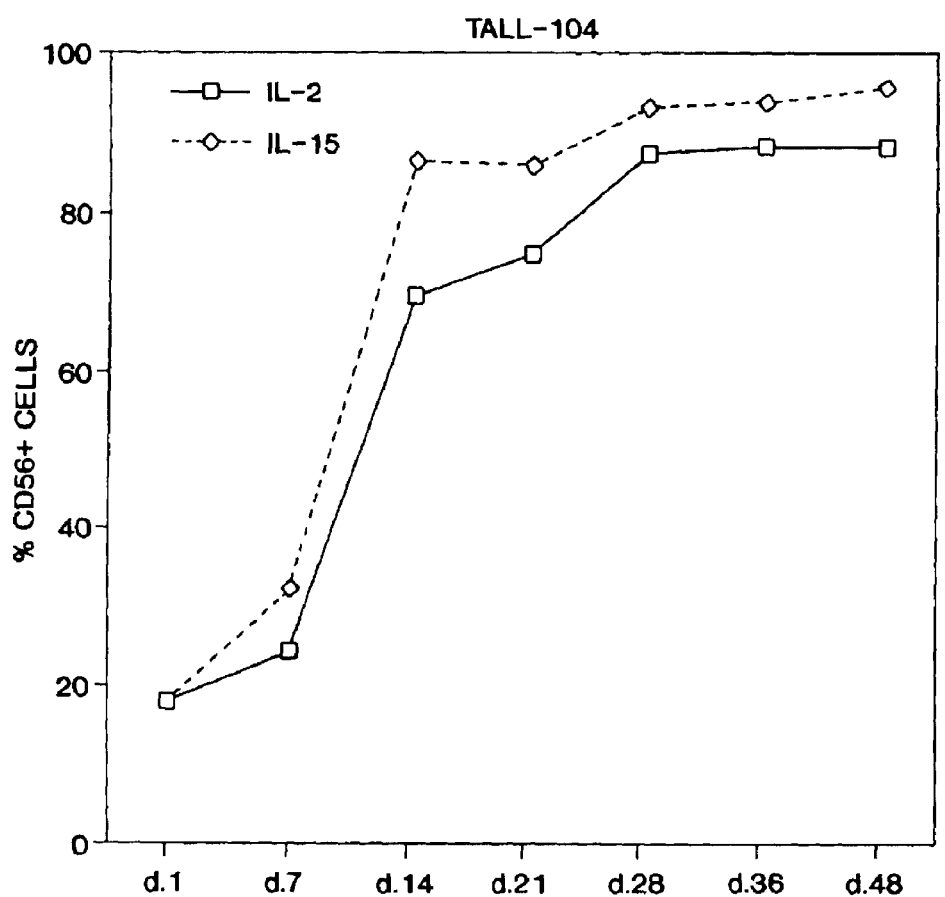
FIG. 3 is a graph indicating that IL-15 induces higher expression of cytotoxic adhesion/activation marker CD56, both as percent of positive cells in the total TALL-104 population and at the single cell level, as the number of molecules present on each cell (higher density). The symbol □ indicates IL-2; the symbol ◊ indicates IL-15. Results are plotted as % CD56+cells over time (days) in culture.
Figure 4:
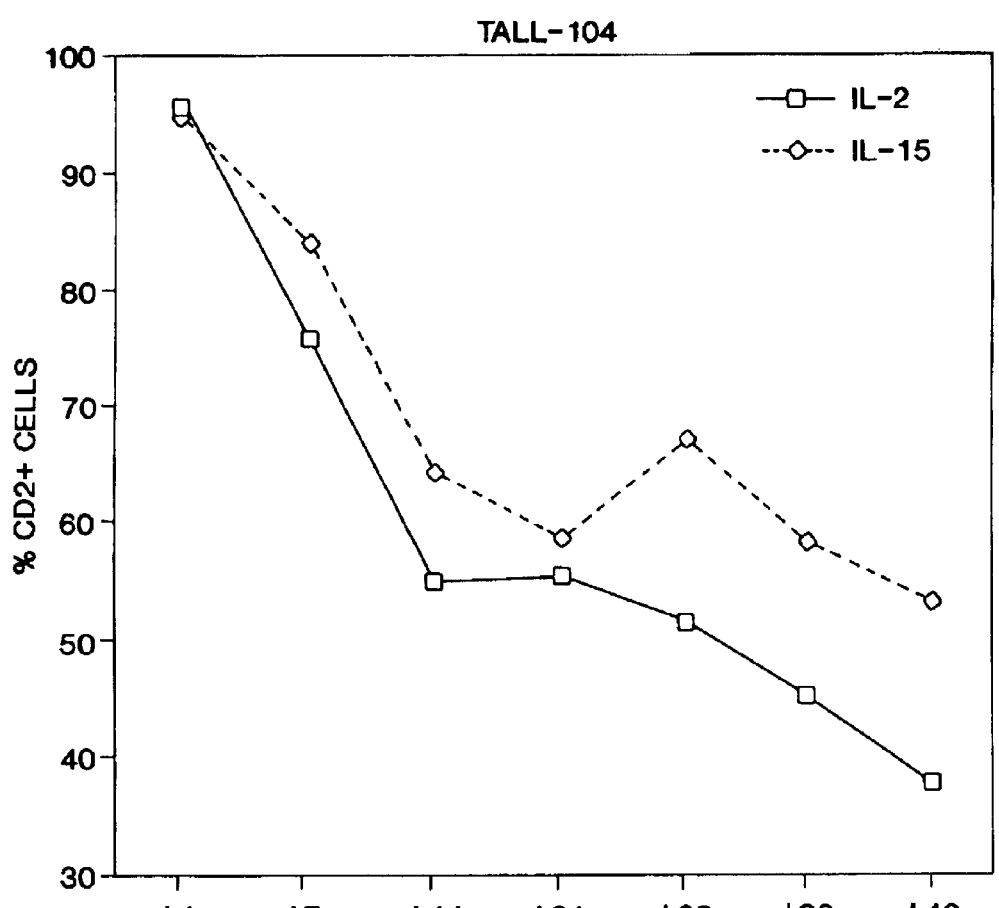
FIG. 4 is a graph demonstrating that undifferentiated TALL-104 cells freshly obtained from the SCID mouse have a higher expression of CD2 and that with time in culture CD2 surface levels decline. However, this decline is slower in TALL-104 cells grown in IL-15 than in IL-2. The symbol 0 indicates IL-2; the symbol 0 indicates IL-15. Results are plotted as % CD2+cells over time (days) in culture.
Figure 5:
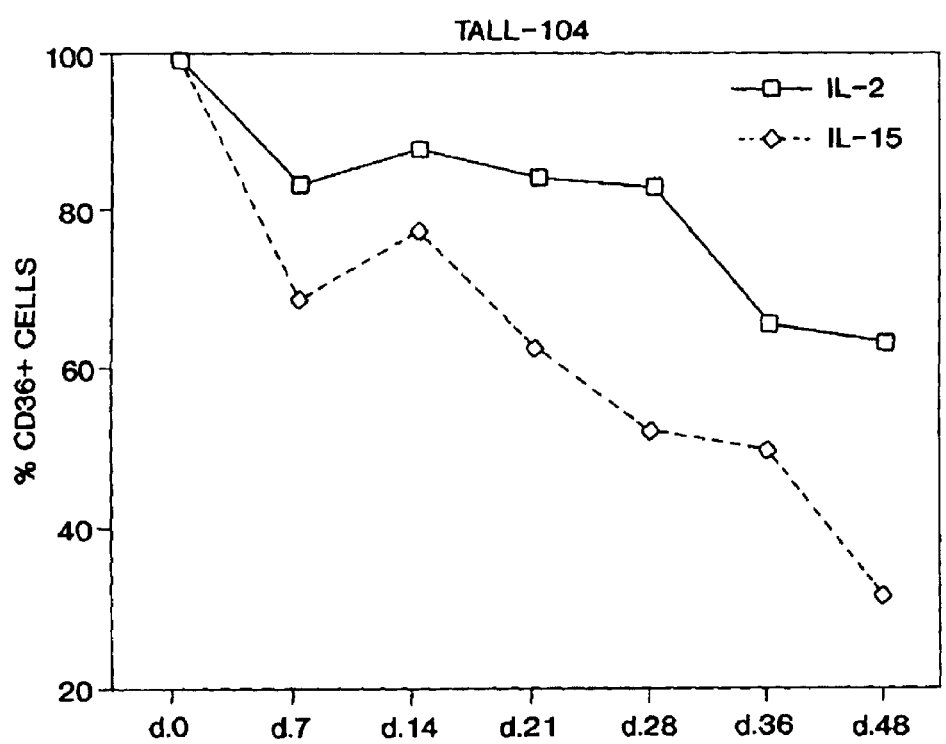
FIG. 5 is a graph demonstrating that TALL-104 cells grown in IL-15 have lower expression of the adhesion molecule CD38. The symbol □ indicates IL-2; the symbol ◊ indicates IL-15. Results are plotted as % CD38+cells over time (days) in culture.

Thus, in one embodiment, TALL-104 cells are prepared as follows. TALL-104 cells (ATCC CRL 11386) are exponentially grown in tissue culture in the presence of recombinant human (rh) IL-15. The resulting proliferation of the cytokine stimulated TALL-104 cells (as measured by $^3$H-TdR uptake) is higher at plateau doses of IL-15 than at plateau doses of IL-2. A "plateau dose" is the dose at which maximal activity is reached, e.g., the optimal dose (see FIG. 1). These cells also demonstrate increased ability to adhere to plastic in vitro (and potentially to endothelium in vivo) by increase in expression of adhesion molecules. These modified TALL-104 cells also demonstrate increased cytotoxic function, as shown by higher levels of killing, increased spectrum of tumor target recognition, and a quicker and more effective kinetic of induction of lytic proteins, such as PFP, SE1 and SE2, and TIA1. Cells grown in an optimal dose of IL-15 generally show higher levels of cytotoxic activity, as compared to the same cells in an optimal dose of IL-2 (see FIG. 2, which demonstrates a significant increase in cytotoxicity against NK-sensitive K562 cells and NK-resistant Raji cells, as compared to the same TALL-104 cells stimulated in IL-2). The cells also demonstrate an increased expression of the cytotoxic adhesion marker CD56 (FIG. 3). TALL-104 cells grown in IL-15 have higher baseline levels of cytokines and respond to stimuli, such as antibodies and target cells, producing higher levels of cytokines than TALL-110 grown in IL-2, with the exception of gamma interferon (IFN-γ), which is produced in higher levels by stimulation of TALL-104 cells in IL-2. The same results were obtained with TALL-103/2 cells.

Therefore, according to one embodiment of this invention, TALL-104 cells may be grown in IL-15 simply to increase the yield thereof, and then grown in IL-2 to reproduce the IL-2 cytotoxic phenotype previously used in clinical therapies for cancer. Alternatively, one may grow TALL-104 cells in IL-15 and use the IL-15 phenotype where enhanced adhesion to endothelium is desired in some clinical applications. The inventors have determined that one may reversibly switch the IL-15 and IL-2 phenotypes of TALL-104 by sequential growth of the cells in one and then the other of these two cytokines, as desired. The biodistribution of the TALL-110 cells may also be affected differently by the two cytokines, based on the different levels of expression of adhesion molecules.

Figure 11:
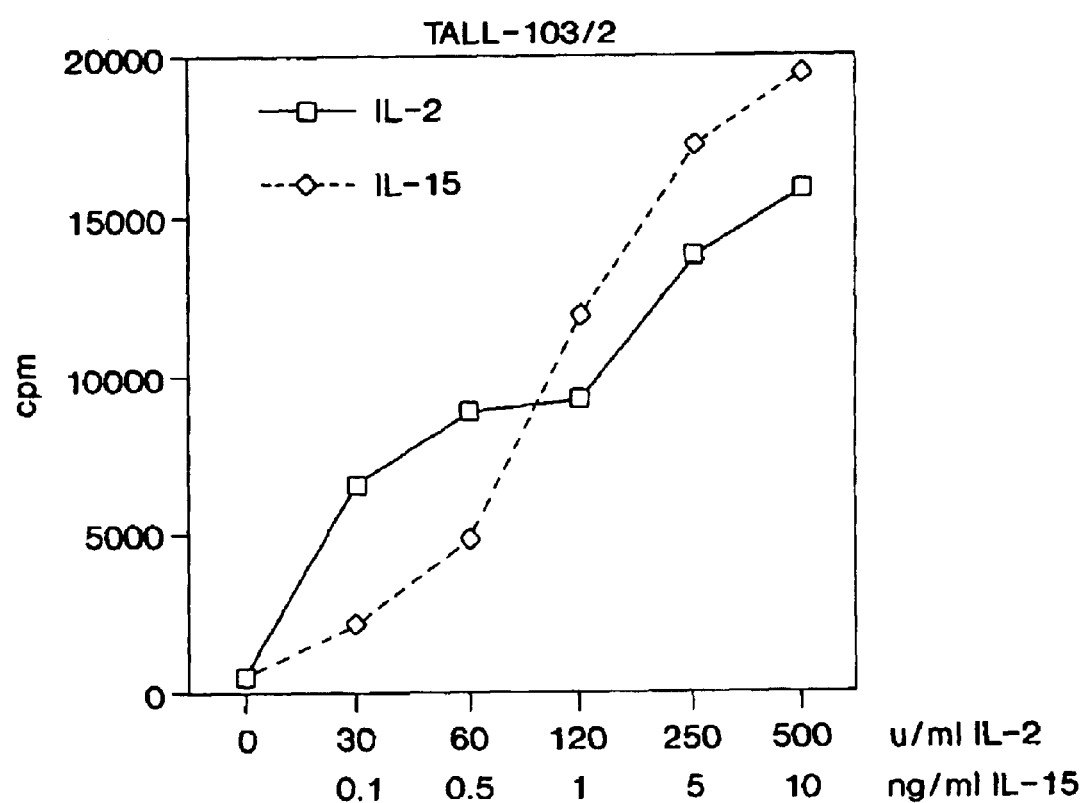
FIG. 11 is a graph which illustrates that IL-15 supports the growth of TALL-103/2 cells in culture. The symbol □ indicates the dosage of IL-2 in U/ml; the symbol ◊ indicates the dosage of IL-15 in ng/ml. Growth of cells is indicated by cpm in $^3$H-TdR proliferation assays. The X-axis shows the concentration of the cytokines.
Figure 12:
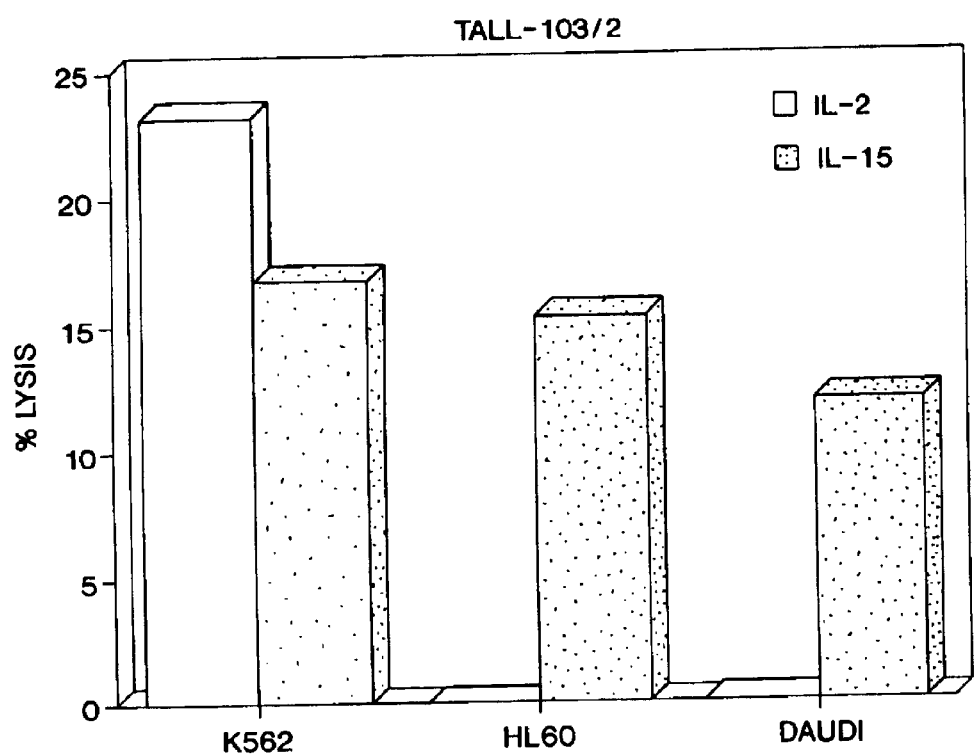
FIG. 12 is a bar graph demonstrating that IL-15 (strippled bars) supports the cytotoxic phenotype of TALL-103/2 cells and broadens the spectrum of target recognition by these cells. The cells were cultured for a week in either IL-15 or IL-2 (clear bars), and then exposed to K562 tumor cells (sensitive target) and H160 or Daudi tumor cells (resistant targets). Cytotoxicity is measured by % lysis of the target cells in $^{51}$Cr release assays.

In yet another embodiment of this invention, TALL-103/2 cells may also be modified by stimulation in IL-15. In this instance, the TALL-103/2 cells will grow more rapidly in culture (FIG. 11) when stimulated with IL-15. Most significantly, when TALL 103/2 cells are stimulated in IL-15, their target recognition expands, and these cells may then be used against more tumor cell types. For example, FIG. 12 shows the results of stimulation of TALL 103/2 cells with IL-15 vs. IL-2. The IL-15 TALL 103/2 cells are able to recognize and kill HL60 and Daudi cells, against which the IL-2 stimulated TALL 103/2 cells were not cytotoxic. Additionally, the stimulation of the TALL 103/2 cells with IL-15 alters the cytokine production by the cells. See, for example, FIGS. 12–16, which showing cytokines that are likely to be involved in the anti-tumor activity of the killer cells. Thus, changing the cytokine profile can result in clinical changes, both in terms of efficacy and/or toxicity.

Based on the effects that IL-15 has on these two cytotoxic T cell lines, it is anticipated that similar effects may be obtained with other cytotoxic T cell lines. Thus, IL-15 may be employed in a method for reversibly altering the phenotype of cytotoxic T cells by culturing said cells in IL-15, thereby obtaining a high yield of a cell having a first phenotype; followed by culturing these cells in IL-2, thereby altering the first phenotype to a second phenotype. The second phenotype may be returned to the first phenotype by further culturing in IL-15 again, if desired. The IL-15 phenotypes are characterized by enhanced growth kinetics, increased cytotoxicity, enhanced cytokine production, and, likely, increased adhesion to vasculature.

These IL-15 stimulated cytotoxic T cells may then be employed in methods for in vivo and ex vivo therapy of cancer, and for other uses for which TALL-104 cells are known, as described in the US patents incorporated by reference above. These modified cells may also be employed as research reagents, as reagents for screening the effect of proposed developmental drugs on their cytotoxic activity, as reagents for the study of their expression of adhesion molecules or cell surface markers, as well as for the production of cytokines or other biological molecules expressed by the modified cells.

The following examples demonstrate the effect of IL-15 on TALL-104 cells and TALL-103/2 cells. These examples in illustrate the preferred methods of the invention. These examples are illustrative only and do not limit the scope of the invention.

EXAMPLE 1

Growth of Tall-104 Cells in IL-15

TALL-104 cells were grown in endotoxin-free Iscove's modified Dulbecco's medium (Gibco-BRL, Grand Island, N.Y.) supplemented with 10% heat-inactivated fetal bovine serum (Sigma) and 100 U/ml rhIL-2 (Chiron Therapeutics, Emeryville, Calif.) or rh IL-15 (1–5 µg/ml) (R& D Systems) in a humidified incubator at 37° C. with 10% $CO_2$ in tissue culture for two weeks.

The cells were then examined for differences in characteristics such as growth, phenotype, cytokine profile, and cytotoxicity, biodistribution and tumor target spectrum of the cultures, and the results were reported in FIGS. 1–10.

A. Proliferation

Figure 1:
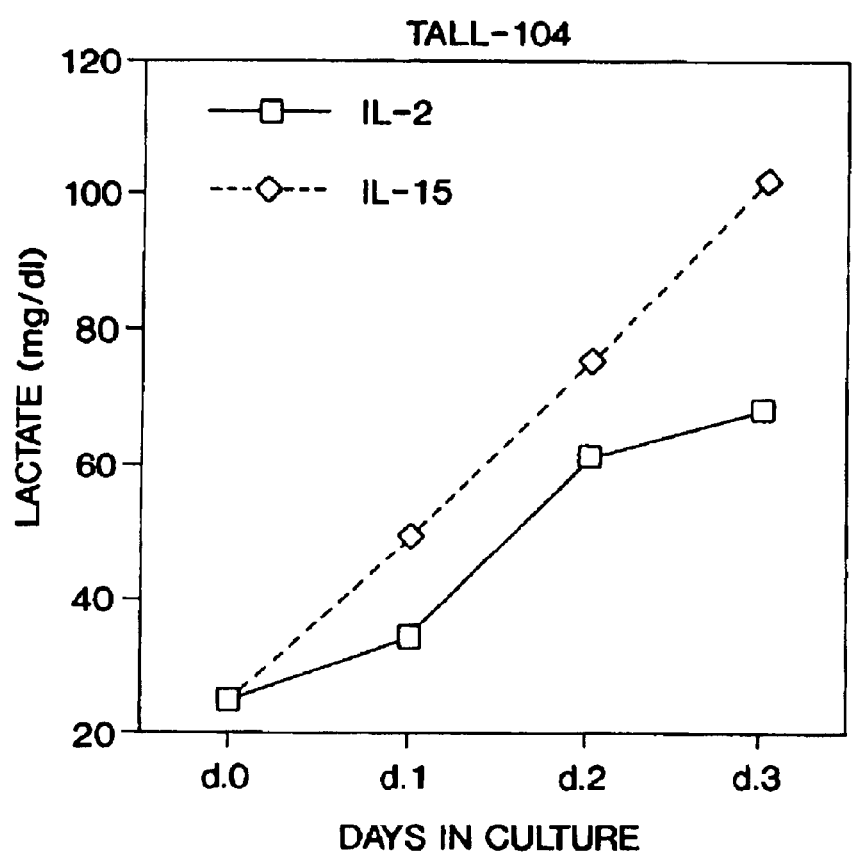
FIG. 1 is a graph which illustrates that IL-15 supports greater TALL-104 cell proliferation in vitro. The symbol □ indicates the 5 ng/ml dosage of IL-15; the symbol ◊ indicates the 100 U/ml dosage of IL-2. Growth of cells is measured by a metabolic surrogate marker, lactate (mg/dl), over days in culture.

As shown in FIG. 1, TALL-104 cells grown in the plateau dose (5 ng/ml) of IL-15 proliferate in vitro faster than do the same cells grown in the plateau dose 100 U/ml) of IL-2.

B. Target Spectrum

In another experiment, the IL-2- or IL-15-treated TALL-104 cells were expanded in vivo in SCID mice and re-adapted to tissue culture conditions. IL-15 induced quicker differentiation of TALL-104 cells into cytotoxic cells in comparison to the effects of IL-2. Undifferentiated TALL-104 cells, extracted from SCID mouse spleens, were cultured for one week with either IL-2 or IL-15, and then tested for cytotoxicity against either K562 or Raji tumor cells. The IL-2-treated TALL-104 cells were only marginally ($\leq 10\%$) cytotoxic, as demonstrated by percent lysis of the tumor cells, for K562 cells. In contrast, the TALL-104 cells stimulated with IL-15 lysed about 40% more K562 tumor cells. The IL-2-treated cells lysed no Raji cells, whereas the IL-15 treated TALL-104 cells lysed almost 60% of these cells. See FIG. 2. The IL-15 treated cells also showed higher levels of cytotoxic molecules, such as perforin, serine esterases (SE) and TIA-1, an apoptosis inducing molecule.

C. Phenotype

TALL-104 cells treated with IL-15 express higher levels of the cytotoxic/adhesion/activation marker CD56, both as percent of positive cells in the total TALL-104 population and at the single cell level, as the number of molecules present on each cell (higher density), than do TALL-104 cells treated with IL-2. See FIG. 3.

Undifferentiated TALL-104 cells freshly obtained from the SCID mice have a high expression of CD2. With time in culture, the CD2 surface levels decline. However, this decline when compared for TALL-104 cells grown in IL-2 or IL-15 as described above, was demonstrated to be slower in the IL-15 stimulated cells. See FIG. 4.

TALL-104 cells grown in IL-15 were also shown to have lower expression of the adhesion molecule CD38 than TALL-104 cells grown in IL-2. See FIG. 5.

D. Cytokine Profile

The TALL-103 cells, grown in either IL-2 or IL-15 as above, were stimulated to trigger cytokine production with OKT3 (anti-CD3), Moon-1 (anti-CD31), or IB4 (anti-CD36) monoclonal antibodies or by exposure to K562 cells.

Figure 6:
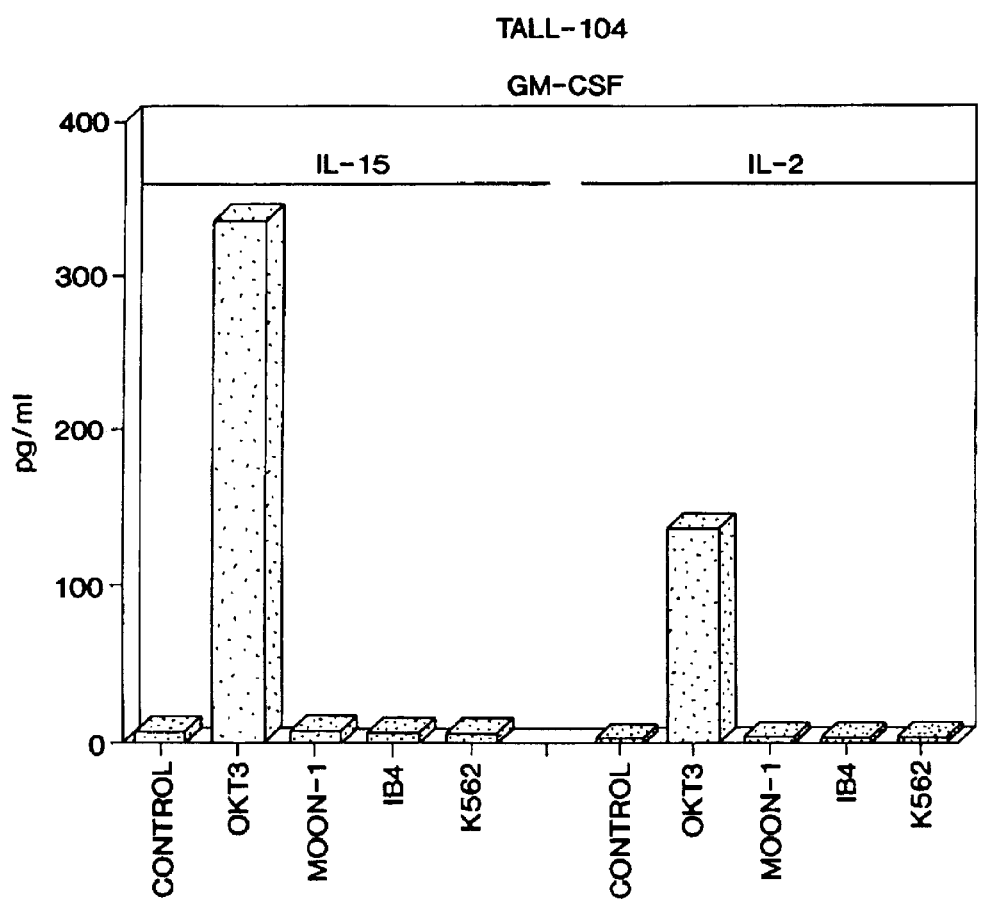
FIG. 6 is a bar graph illustrating the comparative effects of IL-15 and IL-2 on the induction of GM-CSF from TALL-104 cells. On the X axis are the stimuli used to trigger GM-CSF production. The graph shows that TALL-104 cells grown in IL-15 have a baseline level of GM-CSF production, and respond to OKT3 monoclonal antibody with higher production of GM-CSF than cells grown in IL-2.

As seen in FIG. 6, TALL-104 cells grown in IL-15 have a baseline level of GM-CSF production, and respond to OKT3 monoclonal antibody with a significantly higher production of GM-CSF than cells grown in IL-2.

Figure 7:
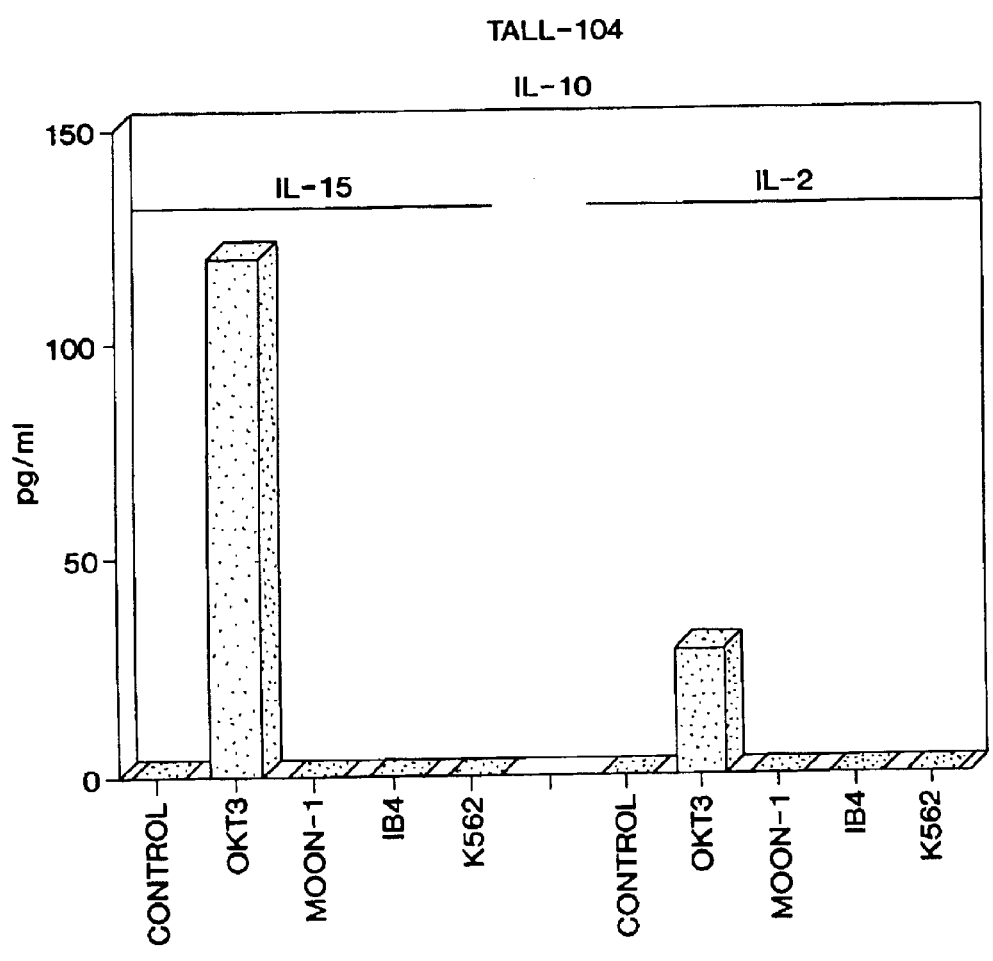
FIG. 7 is a bar graph illustrating the comparative effects of IL-15 and IL-2 on the induction of IL-10 from TALL-104 cells. On the X axis are the stimuli used to trigger IL-10 production. The graph shows that TALL-104 cells grown in IL-15 have a baseline level of IL-10 production, and respond to OKT3 monoclonal antibody with higher production of IL-10 than cells grown in IL-2.

As seen in FIG. 7, TALL-104 cells grown in IL-15 have a baseline level of IL-10 production, and respond to OKT3 monoclonal antibody with significantly higher production of IL-10 than cells grown in IL-2.

Figure 8:
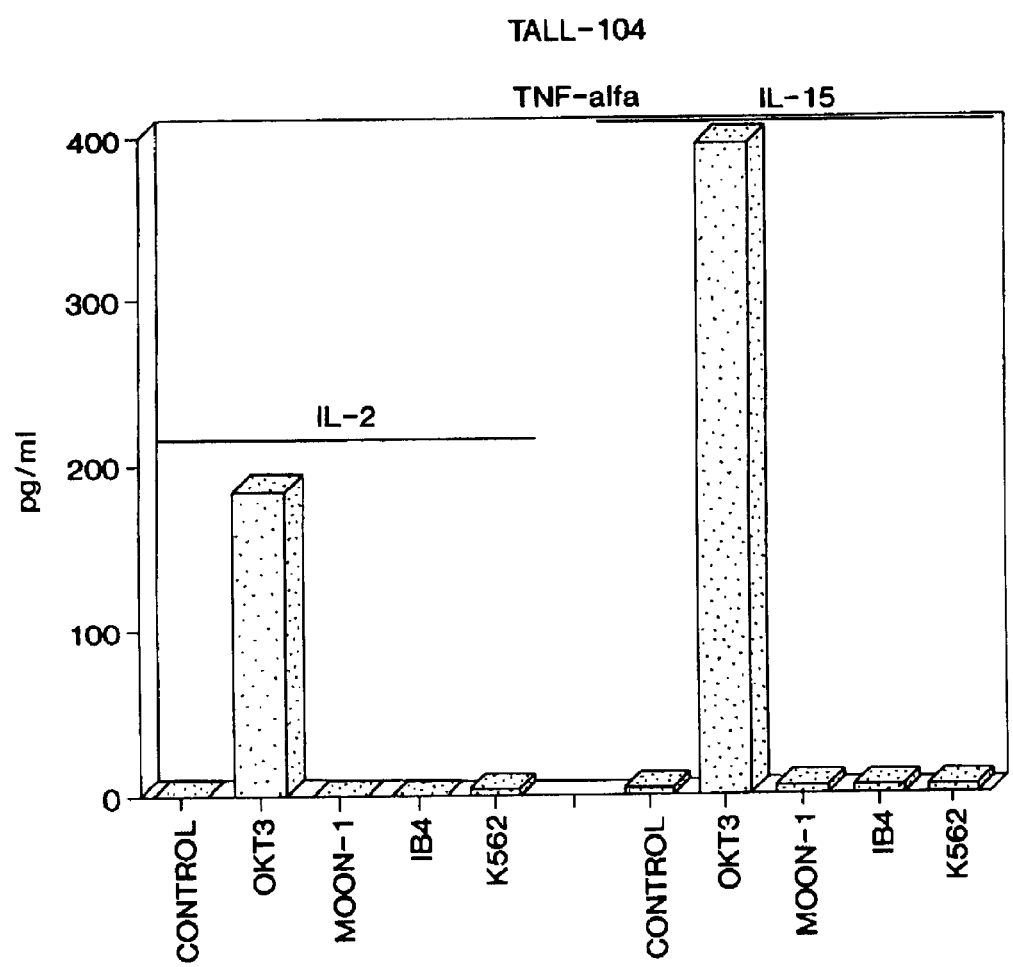
FIG. 8 is a bar graph illustrating the comparative effects of IL-15 and IL-2 on the induction of TNF-α from TALL-104 cells. On the X axis are the stimuli used to trigger TNF-α production. The graph shows that TALL-104 cells grown in IL-15 have a baseline level of TNF-α production, and respond to OKT3 monoclonal antibody with higher production of TNF-α than cells grown in IL-2.

As seen in FIG. 8, TALL-104 cells grown in IL-15 have a baseline level of TNF-α production, and respond to OKT3 monoclonal antibody with higher production of TNF-α than cells grown in IL-2.

Figure 9:
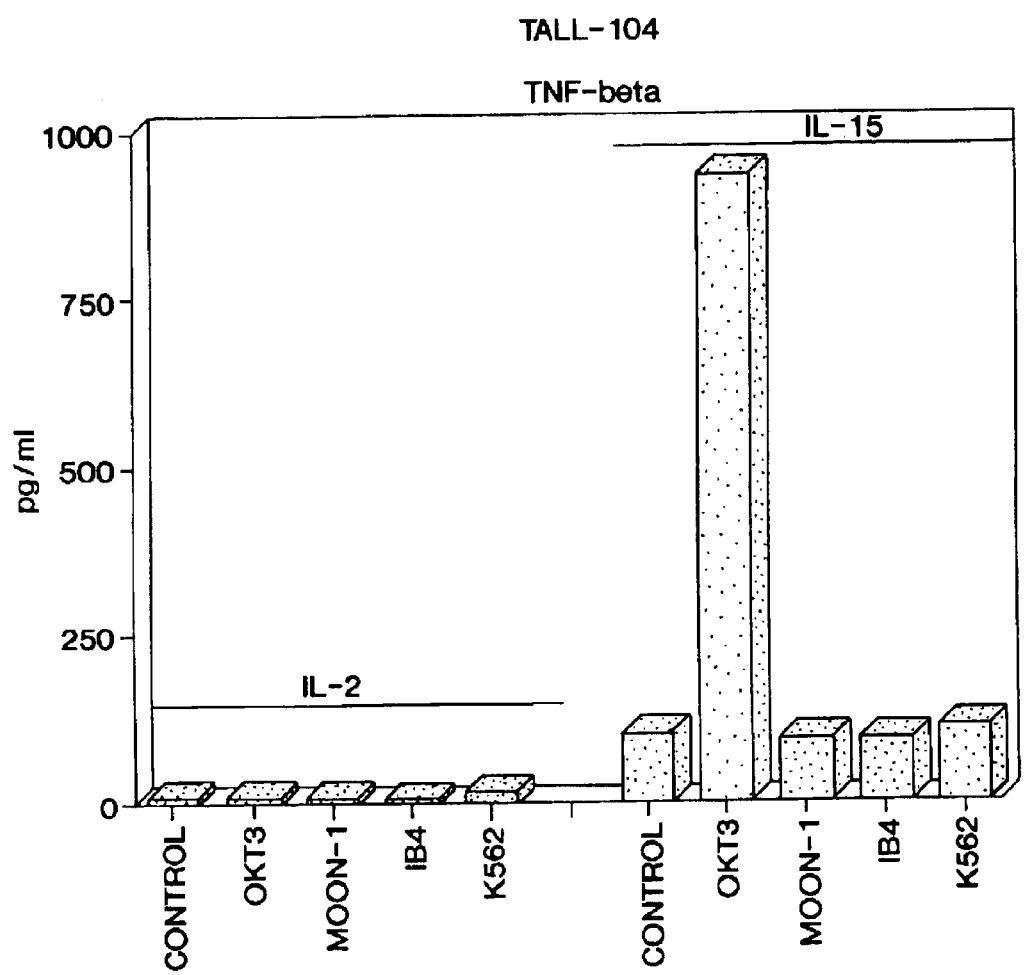
FIG. 9 is a bar graph illustrating the comparative effects of IL-15 and IL-2 on the induction of TNF-β from TALL-104 cells. On the X axis are the stimuli used to trigger TNF-β production. The graph shows that TALL-104 cells grown in IL-15 have a baseline level of TNF-β production, and respond to OKT3 monoclonal antibody with higher production of TNF-β than cells grown in IL-2.

As seen in FIG. 9, TALL-104 cells grown in IL-15 have a baseline level of TNF-β production, and respond to OKT3 monoclonal antibody with higher production of TNF-α than cells grown in IL-2.

Figure 10:
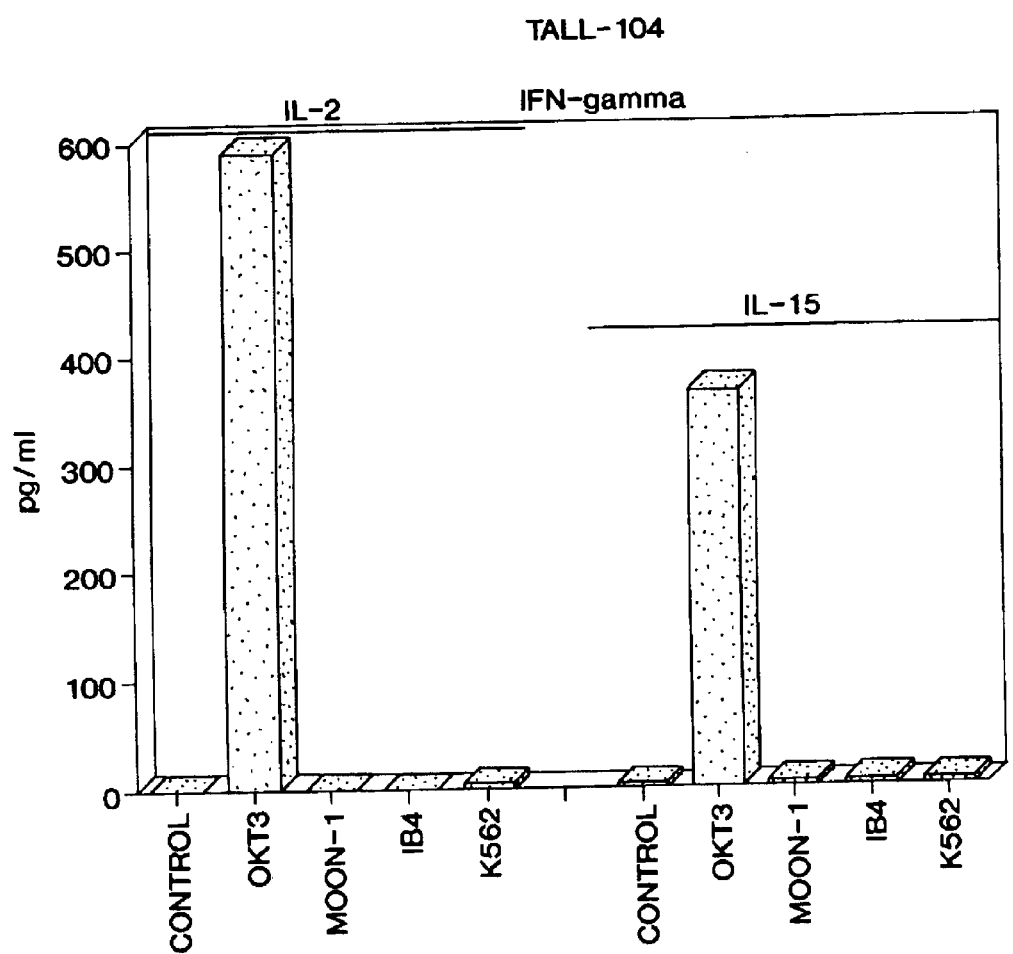
FIG. 10 is a bar graph illustrating the comparative effects of IL-15 and IL-2 on the induction of IFN-γ from TALL-104 cells. On the X axis are the stimuli used to trigger IFN-γ production. The graph shows that TALL-104 cells grown in IL-15 have a baseline level of IFN-γ production, and respond to OKT3 monoclonal antibody with lower production of IFN-γ than cells grown in IL-2.

As seen in FIG. 10, TALL-104 cells grown in IL-15 have a baseline level of IFN-γ production, and respond to OKT3 monoclonal antibody with lower production of IFN-γ than cells grown in IL-2.

EXAMPLE 2

Growth of Tall-103/2 Cells in IL-15

TALL-103/2 cells were grown in endotoxin-free Iscove's modified Dulbecco's medium (Gibco-BRL, Grand Island, N.Y.) supplemented with 10% heat-inactivated fetal bovine serum (Sigma) and 100 U/ml rhIL-2 (Chiron Therapeutics, Emeryvile, Calif.) or rh IL-15 (1–5 µg/ml) [R&D Systems] in a humidified incubator at 37° C. with 10% $C_2$ in tissue culture for two weeks. The cells were then examined for differences in characteristics such as growth, phenotype, cytokine profile, and cytotoxicity, biodistribution and tumor target spectrum of the cultures, and the results were reported in FIGS. 1–10.

A. Phenotype

The surface phenotype of the cultured cells were compared to determine the effect of the two cytokines. The results are reported below in Table I as % positive cells; the mean fluorescence intensity (on a scale with the upper limit of 200) is in parentheses and provides an indication of the antigen density, i.e., the number of molecules/cell.

TABLE I

| Cell Surface Antigen | IL-2 Treated TALL-103/2 | IL-15 Treated TALL-103/2 |
|---|---|---|
| CD3 | 96.5(92) | 35.6(62) |
| CD2 | 53.5(75) | 43.5(61) |
| CD4 | 4.4(60) | 15(62) |
| CD8 | 90.1(131) | 78.9(113) |
| CD56 | 41.6(60) | 67.4(123) |
| LFA-3 | 99.3(125) | 88(118) |
| ICAM-1 | 71.5(84) | 44.9(81) |
| CD45RO | 81.3(83) | 72.2(86) |
| CD38 | 70.5(74) | 32.5(62) |
| CD31 | 35.6(61) | 2.3(66) |

B. Proliferation

In $^3$H-TdR proliferation assays, TALL-103/2 cells grown in IL-15 showed greater proliferation than the cells grown in IL-2 at stimulating cytokine doses greater than 1 ng/ml IL-15. See FIG. 11.

C. Target Spectrum

TALL-103/2 cells were cultured for a week in either IL-15 or IL-2, and then exposed to K562 tumor cells, HL60 tumor cells or Daudi tumor cells. Cytotoxicity was measured by % lysis of the target cells in $^{51}$Cr release assays. As demonstrated in FIG. 12, the IL-15 treated cells caused lysis of all three tumor cell types. The IL-2 treated cells were cytotoxic only for the K562 cells. Thus, the method of this invention supported the cytotoxic phenotype of TALL-103/2 cells and broadened the spectrum of target recognition by these cells.

D. Cytokine Profile

The IL-2-treated and IL-15-treated TALL-103/2 cells were also evaluated for dose-dependent cytokine production. As revealed by FIGS. 13–16, the IL-15 induces production of cytokines from the cells, which is different from that produced by stimulating the cells with IL-2.

Figure 13:
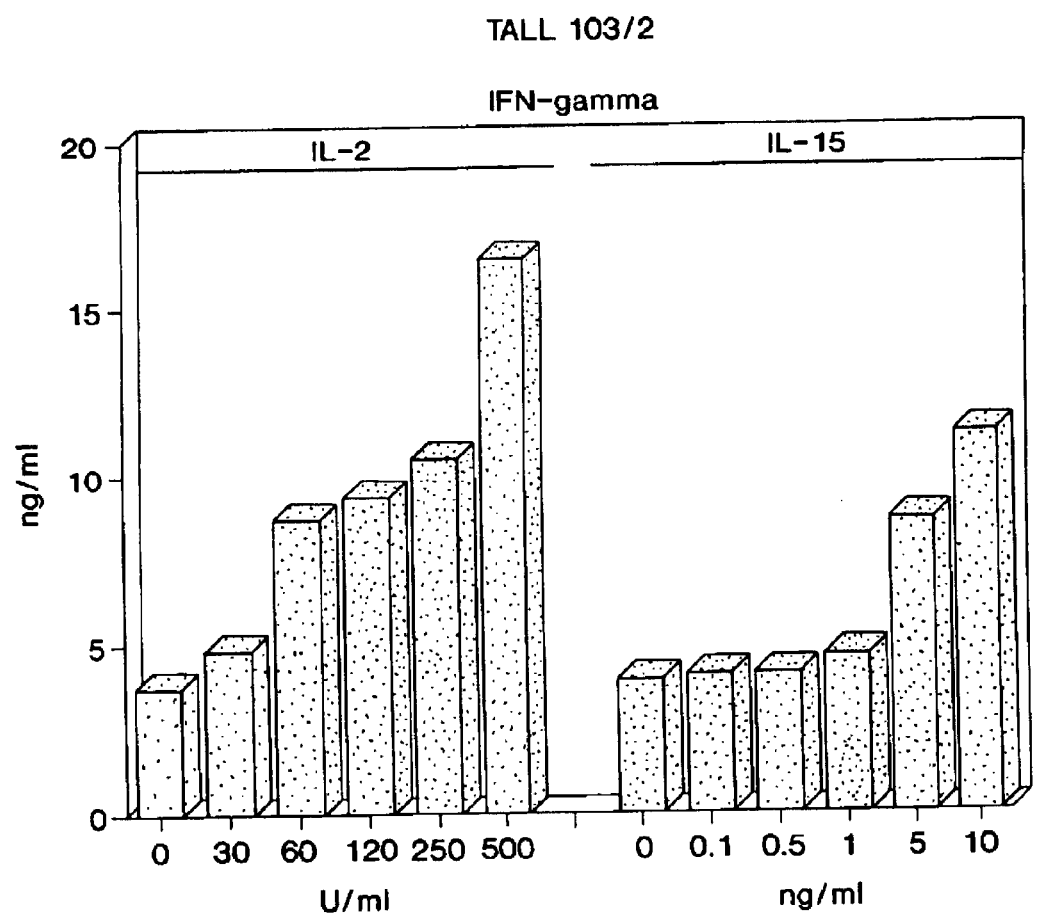
FIG. 13 is a bar graph which illustrates the comparative effect of IL-2 and IL-15 on the induction of IFNγ in TALL-103/2 cells. The X axis shows the cytokine dosage. Results show that IL-2 is a better inducer of this cytokine.
Figure 14:
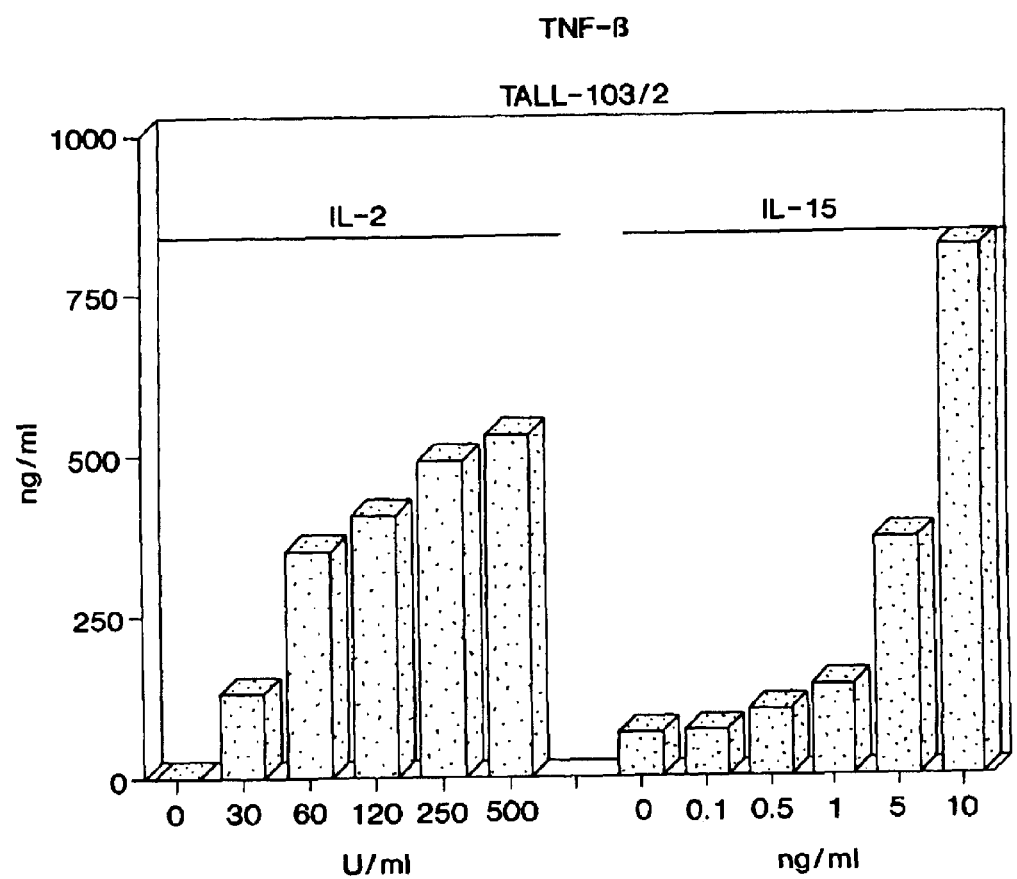
FIG. 14 is a bar graph which illustrates the comparative effect of IL-2 and IL-15 on the induction of TNF-β in TALL-103/2 cells. The X axis shows cytokine dosage. IL-15 induces higher levels of TNF-β at the concentration of 10 μg/ml.

IL-2 stimulation induces better expression of IFNγ in TALL-103/2 cells, than does IL-15 stimulation (FIG. 13).

IL-15 induces higher levels of TNF-β at the concentration of 10 μg/ml (FIG. 14), than does IL-2 stimulation.

Figure 15:
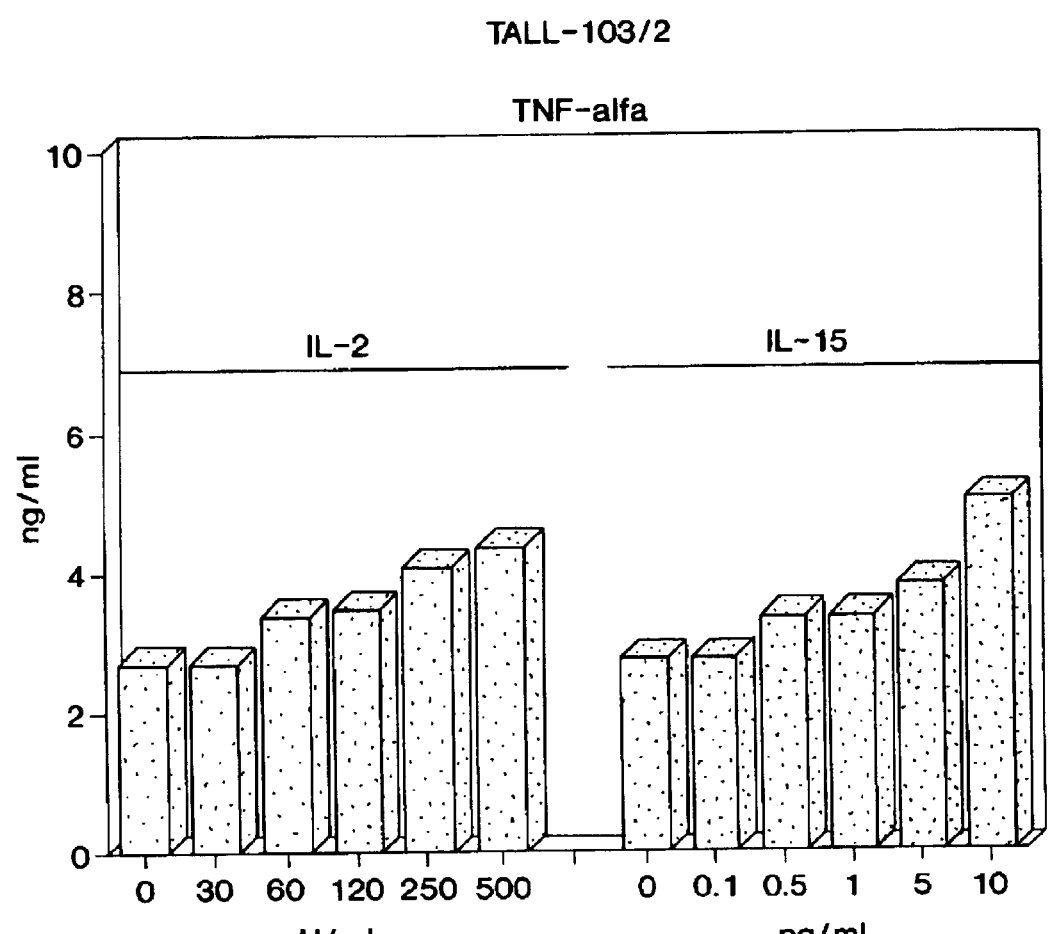
FIG. 15 is a bar graph which illustrates the comparative effect of IL-2 and IL-15 on the induction of TNF-α in TALL-103/2 cells. Similar levels of TNF-α are induced by the two cytokines.

Similar levels of TNF-α are induced by the two cytokines (FIG. 15).

Figure 16:
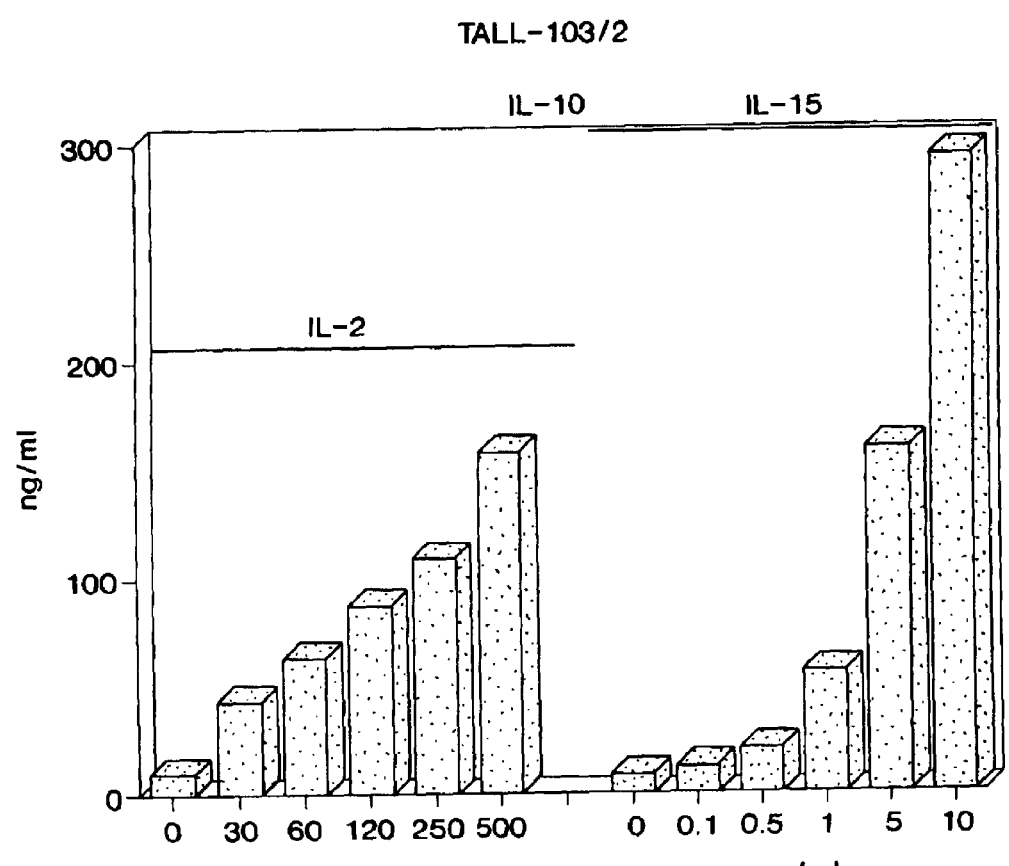
FIG. 16 is a bar graph which illustrates the comparative effect of IL-2 and IL-15 on the induction of IL-10 in TALL-103/2 cells. IL-15 is a better inducer of IL-10 as compared to IL-2.

IL-15-stimulated TALL-103/2 cells produce greater amounts of IL-10 at concentrations over 10 ng/ml IL-15 (FIG. 16).

Numerous modifications and variations of the present invention are included in the above-identified specification and are expected to be obvious to one of skill in the art. Such modifications and alterations to the methods of the present invention are believed to be encompassed in the scope of the claims appended hereto.

What is claimed is:

1. A method of modifying TALL-104 cells (ATCC CRL 11386) comprising:

culturing TALL-104 cells in an effective amount of IL-15, wherein said cells grow at a rate faster than when stimulated by IL-2, and have an altered phenotypic, cytotoxic and cytokine profile.

2. The method according to claim 1 wherein said modified cells have an increased level of cytotoxicity.

3. The method according to claim 1, wherein said modified cells demonstrate a change in a characteristic selected from the group consisting of increased proliferation, differentiation, growth, phenotype, adhesion molecule expression, biodistribution, cytokine production profile, and tumor target spectrum.

4. The method according to claim 3 wherein said cytokine production profile is characterized by increased expression of IL-10, increased expression of GM-CSF, increased expression of TNF-α, increased expression of TNF-β, and decreased expression of gamma interferon upon stimulation with anti-CD3 antibody.

5. The method according to claim 3 wherein said phenotype is characterized by increased expression of the cytotoxic adhesion/activation marker CD56 and decreased expression of the adhesion molecule CD38.

* * * * *